(12) United States Patent  
Lin

(10) Patent No.: US 6,716,210 B2
(45) Date of Patent: *Apr. 6, 2004

(54) REFRACTIVE SURGICAL LASER APPARATUS AND METHOD

(75) Inventor: Jui-Teng Lin, Winter Springs, FL (US)

(73) Assignee: LaserSight Technologies, Inc., Winter Park, FL (US)

( * ) Notice: Subject to any disclaimer, the term of this patent is extended or adjusted under 35 U.S.C. 154(b) by 192 days.

This patent is subject to a terminal disclaimer.

(21) Appl. No.: 09/826,843

(22) Filed: Apr. 6, 2001

(65) Prior Publication Data

US 2001/0037105 A1 Nov. 1, 2001

Related U.S. Application Data

(63) Continuation of application No. 08/961,133, filed on Oct. 30, 1997, now abandoned, which is a continuation of application No. 08/489,497, filed on Jun. 12, 1995, now abandoned, which is a continuation-in-part of application No. 08/218,319, filed on Mar. 25, 1994, now Pat. No. 5,520,679, which is a continuation-in-part of application No. 07/985,617, filed on Dec. 3, 1992, now abandoned.

(51) Int. Cl.$^7$ ............................................... A61B 18/18
(52) U.S. Cl. ................................. 606/5; 606/4; 128/898
(58) Field of Search ............................. 606/2–6, 10–12; 128/898

(56) References Cited

U.S. PATENT DOCUMENTS

| 2,480,737 A | 8/1949 | Jayle |
| 3,074,407 A | 1/1963 | Moon |
| 3,476,112 A | 11/1969 | Elstein |
| 3,697,889 A | 10/1972 | Dewey, Jr. |
| 3,743,965 A | 7/1973 | Offner |
| 3,848,104 A | 11/1974 | Locke |
| 3,938,058 A | 2/1976 | Yamamoto |
| 3,982,541 A | 9/1976 | L'Esperance, Jr. |
| 3,983,507 A | 9/1976 | Tang et al. |
| 4,169,663 A | 10/1979 | Murr |

(List continued on next page.)

FOREIGN PATENT DOCUMENTS

| CA | 1243732 | 10/1984 |
| EP | 0 151869 A2 | 8/1985 |
| EP | 0296982 A1 | 6/1988 |
| EP | 0151869 B1 | 1/1990 |
| EP | 0368512 A2 | 5/1990 |

(List continued on next page.)

OTHER PUBLICATIONS

Ren et al, "Corneal Refractive Surgery . . . Solid State Laser" Ophthalmic Tech, Jun. 1991, pp129–139.*

Qiushi Ren, et al. "Corneal Refractive Surgery Using An Ultra–Violet (213 nm) Solid State Laser." Ophthalmic Technologies, vol. 1423 (1991), p. 129–139.

(List continued on next page.)

Primary Examiner—Michael Peffley

(57) ABSTRACT

A scanning ablation laser is disclosed having a fundamental output from a mirrored facet in the ultraviolet range, the fundamental ultraviolet output having an energy level of no greater than 10 mJ/pulse on the corneal surface. A controller controls the laser and scanning mechanism to deliver a focused and scanned pulsed output laser beam in a predetermined overlapping pattern onto a plurality of positions on a corneal surface to photoablate at least one layer of corneal tissue such that an overlap among respective ablating spots of individual pulses of the scanned pulsed output laser beam on a single ablation layer is at least 50%. The scanning mechanism may locate laser beam pulses in a random pattern on the corneal surface. In one embodiment, a beam splitter splits the pulsed output laser beam into a plurality of laser beams.

12 Claims, 2 Drawing Sheets

U.S. PATENT DOCUMENTS

| | | |
|---|---|---|
| 4,180,751 A | 12/1979 | Ammann |
| 4,349,907 A | 9/1982 | Campillo et al. |
| 4,386,428 A | 5/1983 | Bauer |
| 4,423,728 A | 1/1984 | Lieberman |
| 4,461,294 A | 7/1984 | Baron |
| 4,477,159 A | 10/1984 | Mizuno et al. |
| 4,520,816 A | 6/1985 | Schachar et al. |
| 4,526,171 A | 7/1985 | Schachar |
| 4,538,608 A | 9/1985 | L'Esperance, Jr. |
| 4,546,773 A | 10/1985 | Kremer et al. |
| 4,573,467 A | 3/1986 | Rich et al. |
| 4,580,559 A | 4/1986 | L'Esperance, Jr. |
| 4,598,714 A | 7/1986 | Kremer et al. |
| 4,619,259 A | 10/1986 | Graybill et al. |
| 4,633,866 A | 1/1987 | Peyman et al. |
| 4,653,495 A | 3/1987 | Nanaumi |
| 4,662,370 A | 5/1987 | Hoffmann et al. |
| 4,665,913 A | 5/1987 | L'Esperance, Jr. |
| 4,669,466 A | 6/1987 | L'Esperance, Jr. |
| 4,688,570 A | 8/1987 | Kramer et al. |
| 4,718,418 A | 1/1988 | L'Esperance, Jr. |
| 4,720,189 A | 1/1988 | Heynen et al. |
| 4,721,379 A | 1/1988 | L'Esperance, Jr. |
| 4,729,372 A | 3/1988 | L'Esperance, Jr. |
| 4,729,373 A | 3/1988 | Peyman |
| 4,732,148 A | 3/1988 | L'Esperance, Jr. |
| 4,764,930 A | 8/1988 | Bille et al. |
| 4,770,172 A | 9/1988 | L'Esperance |
| 4,773,414 A | 9/1988 | L'Esperance, Jr. |
| 4,784,135 A | 11/1988 | Blum et al. |
| 4,798,204 A | 1/1989 | L'Esperance, Jr. |
| 4,807,623 A | 2/1989 | Lieberman |
| 4,838,266 A | 6/1989 | Koziol et al. |
| 4,838,679 A | 6/1989 | Bille |
| 4,840,175 A | 6/1989 | Peyman |
| 4,848,340 A | 7/1989 | Bille et al. |
| 4,856,513 A | 8/1989 | Muller |
| 4,862,886 A | 9/1989 | Clarke et al. |
| 4,896,015 A | 1/1990 | Taboada et al. |
| 4,901,718 A | 2/1990 | Bille et al. |
| 4,903,695 A | 2/1990 | Warner et al. |
| 4,907,586 A | 3/1990 | Bille et al. |
| 4,911,711 A | 3/1990 | Telfair et al. |
| 4,925,523 A | 5/1990 | Braren et al. |
| 4,941,093 A | 7/1990 | Marshall et al. |
| 4,968,130 A | 11/1990 | Hideshima et al. |
| 4,975,918 A | 12/1990 | Morton |
| 4,993,826 A | 2/1991 | Yoder, Jr. |
| 4,994,058 A | 2/1991 | Raven et al. |
| 5,019,074 A | 5/1991 | Muller |
| 5,052,004 A | 9/1991 | Gratze et al. |
| 5,063,942 A | 11/1991 | Kilmer et al. |
| 5,065,046 A | 11/1991 | Guyer |
| 5,074,859 A | 12/1991 | Koziol |
| 5,102,409 A | 4/1992 | Balgorod |
| 5,108,388 A | 4/1992 | Trokel |
| 5,108,412 A | 4/1992 | Krumeich et al. |
| 5,133,726 A | 7/1992 | Ruiz et al. |
| 5,144,630 A * | 9/1992 | Lin .......................... 359/330 |
| 5,163,934 A | 11/1992 | Munnerlyn |
| 5,163,936 A | 11/1992 | Black et al. |
| 5,182,759 A | 1/1993 | Anthon et al. |
| 5,188,631 A | 2/1993 | L'Esperanace, Jr. |
| 5,196,006 A | 3/1993 | Klopotek et al. |
| 5,207,668 A | 5/1993 | L'Esperance, Jr. |
| 5,217,452 A | 6/1993 | O'Donnell |
| 5,219,343 A | 6/1993 | L'Esperance, Jr. |
| 5,219,344 A | 6/1993 | Yoder, Jr. |
| 5,222,960 A | 6/1993 | Poley |
| 5,226,903 A | 7/1993 | Mizuno |
| 5,250,062 A | 10/1993 | Hanna |
| 5,257,988 A | 11/1993 | L'Esperance, Jr. |
| 5,263,950 A | 11/1993 | L'Esperance, Jr. |
| 5,280,491 A * | 1/1994 | Lai .......................... 359/347 |
| 5,284,477 A | 2/1994 | Hanna et al. |
| 5,288,292 A | 2/1994 | Giraud et al. |
| 5,290,301 A | 3/1994 | Lieberman |
| 5,312,320 A | 5/1994 | L'Esperance, Jr. |
| 5,324,281 A | 6/1994 | Muller |
| 5,334,190 A | 8/1994 | Seiler |
| 5,336,217 A | 8/1994 | Buys et al. |
| 5,345,534 A | 9/1994 | Najm et al. |
| 5,349,590 A | 9/1994 | Amirkhanian et al. |
| 5,350,374 A | 9/1994 | Smith |
| 5,353,262 A | 10/1994 | Yakymyshyn et al. |
| 5,360,424 A | 11/1994 | Klopotek |
| 5,363,388 A | 11/1994 | Shi et al. |
| 5,364,388 A | 11/1994 | Koziol |
| 5,370,641 A | 12/1994 | O'Donnell, Jr. |
| 5,395,356 A | 3/1995 | King et al. |
| 5,395,362 A | 3/1995 | Sacharoff et al. |
| 5,405,355 A | 4/1995 | Peyman et al. |
| 5,411,501 A | 5/1995 | Klopotek |
| 5,423,801 A | 6/1995 | Marshall et al. |
| 5,425,727 A | 6/1995 | Koziol |
| 5,425,729 A | 6/1995 | Ishida et al. |
| 5,437,658 A | 8/1995 | Muller et al. |
| 5,441,511 A | 8/1995 | Hanna |
| 5,442,487 A | 8/1995 | Mizuno |
| 5,445,633 A | 8/1995 | Nakamura et al. |
| 5,461,212 A | 10/1995 | Seiler et al. |
| 5,470,329 A | 11/1995 | Sumiya |
| 5,474,548 A | 12/1995 | Knopp et al. |
| 5,480,396 A | 1/1996 | Simon et al. |
| 5,505,723 A | 4/1996 | Muller |
| 5,507,741 A | 4/1996 | L'Esperance, Jr. |
| 5,507,799 A | 4/1996 | Sumiya |
| 5,520,679 A | 5/1996 | Lin |
| 5,549,597 A | 8/1996 | Shimmick et al. |
| 5,556,395 A | 9/1996 | Shimmick et al. |
| 5,582,752 A | 12/1996 | Zair |
| 5,599,340 A | 2/1997 | Simon et al. |
| 5,613,965 A | 3/1997 | Muller |
| 5,624,436 A | 4/1997 | Nakamura et al. |
| 5,634,920 A | 6/1997 | Hohla |
| 5,637,109 A | 6/1997 | Sumiya |
| 5,646,791 A | 7/1997 | Glockler |
| 5,651,784 A | 7/1997 | Klopotek |
| 5,683,379 A | 11/1997 | Hohla |
| 5,684,562 A | 11/1997 | Fujieda |
| 5,711,762 A | 1/1998 | Trokel |
| 5,713,892 A | 2/1998 | Shimmick |
| 5,735,843 A | 4/1998 | Trokel |
| 5,782,822 A | 7/1998 | Telfair et al. |
| 5,849,006 A | 12/1998 | Frey et al. |
| 5,865,830 A | 2/1999 | Parel et al. |
| 6,210,401 B1 * | 4/2001 | Lai .......................... 606/12 |
| 6,325,792 B1 * | 12/2001 | Swinger et al. .......... 606/11 |
| RE37,504 E * | 1/2002 | Lin .......................... 128/898 |

FOREIGN PATENT DOCUMENTS

| | | |
|---|---|---|
| EP | 0207648 B1 | 8/1990 |
| EP | 0418890 A3 | 3/1991 |
| EP | 0602756 A1 | 6/1994 |
| WO | PCT/FR87/00139 | 11/1987 |
| WO | PCT/US92/09625 | 5/1993 |
| WO | PCT/US93/00327 | 8/1993 |
| WO | PCT/US94/02007 | 9/1994 |
| WO | PCT/EP95/01287 | 10/1995 |

OTHER PUBLICATIONS

Shui Lai. "Method and Apparatus for Surgery of the Cornea Using Short Laser Pulses Having Shallow Ablation Depth." Publication No. 2001/0010003, Jul. 2001.

Qiushi Ren, Raymond P. Galitis, Keith P. Thompson, & J.T. Lin, "Ablation of the Cornea and Synthetic Polymers Using a UV (213 nm) Solid State Laser", IEEE Journal of Quatum Electronics, Dec. 1990, pp. 2284–2288.

Conference on Lasers and Electro–Optics, Optical Society of America, May 1990, pp. 28–30.

G.P.A. Malcom, M.A. Persaud, & A.I. Ferguson, "Resonant Frequency Quadrupling of a Mode—Locked Diode—Pumped Nd: YLF Laser", Optics Letters, Jul. 1991, pp. 983–985.

J.T. Lin, J.L. Montgomery, "Temperature—Tuned Noncritically Phase—Matched Frequency Conversion in $LiB_3O_5$ Crystal", Optics Communications, Dec. 1990, pp. 159–165.

A.A. Babin, F.I. Fel'dshtein, & I.V. Yakovlev, "Generation of the Fifth Harmonic of Yttrium Orthoaluminate: $Nd^{3+}$ Laser Radiation in KDP at Room Temperature", Soviet Technical Physics Letters, Jun. 1990, pp. 417–418.

V.D. Volosov & E.V. Nilov, "Effect of the Spatial Structure of a Laser Beam on the Generation of the Second Harmonic in ADP and KDP Crystals", UDC, Nov. 1965, pp. 715–719.

A.G. Arutyunyan, G.G. Gurzadyan, & R.K. Ispiryan, "Generation of the Fifth Harmonic of Picosecond Yttrium Aluminate Laser Radiation", Soviet Journal Quantum Electron, Dec. 1989, pp. 1602–1603.

Shinichi Imai, Toshitaka Yamada, Yasutomo Fujimori & Ken Ishikawa, Third—Harmonic Generation of an Alexandrite Laser in $\beta$–$BaB_2O_4$, Applied Physics Letters, May 1989, pp. 1206–1208.

Conference on Lasers and Electro–Optics, Optical Society of America, Apr. 1989, p. 390.

Barraquer, "Lamellar Keratoplasty (special techniques)" Annals of Ophthalmology, Jun. 1972, pp. 437–469.

Burnett, "Company Denies Delay in Approval for Laser", Orlando Sentinel, Feb. 1993, pp. 12–13.

Burnett, "Medical Technology", Orlando Sentinel, Feb. 1993, pp. 1–5.

Gailitis et al., "Solid State Ultraviolet Laser (213 nm) Ablation of the Cornea and Synthetic Collagen Lenticules", Lasers in Surgery and Medicine, Dec. 1991, pp. 556–562.

Gartry et al., "Excimer Laser Photorefractive Keratectomy", Ophthalmology, Aug. 1992, pp. 1210–1219.

Gilbert, "Corneal Topography: In Search of the Excimer Islands", Eye Care Technology, Oct. 1993, pp. 23–28.

L'Esperance, "New Laser Systems, Their Potential Clinical Usefulness, and Investigative Laser Procedures", Ophthalmic Lasers, 1989, pp. 995–1045.

Lin et al, "Corneal Topography Following Excimer Photorefractive Kerectomy for Myopia", Journal of Cataract Refractive Surgery, 1993, pp. 149–154.

Lin et al, "A Multiwavelength Solid State Laser for Ophthalmic Applications", Ophthalmic Technologies, Jun. 1992, pp. 266–275.

Marguerite B. McDonald et al, "Central Photorefractive Keratectomy for Myopia", Ophthalmology, Sep. 1991, pp. 1327–1337.

Marshall et al, "Long–term Healing of the Central Cornea after Photorefractive Keratectomy Using an Excimer Laser", Oct. 1998, pp. 1411–1421.

Marshall et al, "Photoablative Reprofiling of the Cornea Using an Excimer Laser: Photorefractive Keratectomy", Lasers in Ophthalmology, Jan. 1986, pp. 21–48.

McDonald et al., "Central Photorefractive Keratectomy for Myopia", Arch Ophthalmology, Jun. 1990, pp. 799–808.

Palikaris et al, "Excimer Laser in Situ Keratomileusis and Photorefractive Keratectomy for Correction of High Myopia", Journal of Refractive and Corneal Surgery, Sep. 1994, pp. 498–510.

Ren et al, "Corneal Refractive Surgery Using an Ultra–Violet (213nm) Solid State Laser" Ophthalmic Technologies, Jun. 1991, pp. 129–139.

Rozakis, "Refractive Lamellar Keratoplasty" History of Keratomileusis, 1994, Chapt. 1–13.

Seiler et al, "Excimer Laser (193nm) Myopic Keratomileusis in Sighted and Blind Human Eyes" Refracitve and Corneal Laser Surgery, Jun. 1990, pp. 165–173.

Serdarevic, "Corneal Laser Surgery", Ophthalmic Lasers, 1989, pp. 919–970.

Steinert et al, "Laser Corneal Surgery", Laser Research Laboratory, 1998, pp. 151–154.

Thompson et al, "Philosophy and Technique for Excimer Laser Phototheraputic Keratectomy", Refractive and Corneal Surgery, Apr. 1993, pp. 81–85.

Trokel et al Excimer Laser Surgery of the Cornea, American Journal of Ophthalmology, Dec. 1983, pp. 710–715.

Trockel et al, "Evolution of Excimer Laser Corneal Surgery", Jul. 1989, pp. 373–381.

Van Mielaert et al, "On the Safety of 193–Nanometer Excimer Laser Refractive Corneal Surgery" Refractive and Corneal Surgery, Jun. 1992, pp. 235–239.

Wilson et al, "Changes in Corneal Topography after Excimer Laser Photorefractive Keratectomy for Myopia", Ophthalmology, Sep. 1991, pp. 1338–1347.

* cited by examiner

US 6,716,210 B2

REFRACTIVE SURGICAL LASER APPARATUS AND METHOD

This application is a continuation of co-pending application Ser. No. 08/961,133, filed Oct. 30, 1997, now abandoned the entirety of which is explicitly incorporated herein by reference, which is a continuation of application Ser. No. 08/489,497, filed Jun. 12, 1995, now abandoned, which is a continuation-in-part of application Ser. No. 08/218,319, filed Mar. 25, 1994, now U.S. Pat. No. 5,520,679, which is a continuation-in-part of application Ser. No. 07/985,617, filed Dec. 3, 1992, now abandoned.

BACKGROUND OF THE INVENTION

1. Field of the Invention

The present invention relates to refractive surgical methods using lasers and software-driven scanning mechanisms for utility corneal reshaping by procedures of photorefractive keratectomy(PRK) and laser in situ keratomileusis (LASIK).

2. Prior Art

Various lasers have been used for ophthalmic applications including the treatments of glaucoma, cataract and refractive surgery. For non-refractive treatments suitable laser wavelengths are in the ranges of visible to near infrared. They include: Nd:YAG (1064 nm), doubled-YAG (532 nm), argon (488, 514 nm), krypton (568, 647 nm), semiconductor lasers (630–690 nm and 780-860 nm) and tunable dye lasers (577–630 nm). For refractive surgeries (or corneal reshaping), ultraviolet (UV) ArF lasers (at 193 nm) have been used for large area surface corneal ablation in a process called photorefractive keratectomy(PRK). Corneal reshaping may also be performed by laser thermal coagulation currently conducted by Ho:YAG lasers which however, has very limited long term clinical results.

The existing ArF excimer lasers have drawbacks of being large in size and weight, using toxic gas and high maintenance cost.

The existing non-excimer UV laser systems include (a) argon-pumped Ti:sapphire and (b) fifth-harmonic of flash lamp pumped Nd:YAG. System (a) is limited by high-cost and the life-time of the argon laser which is a bulky gas laser. System (b) is patented by the present inventor, J. T. Lin, (U.S. Pat. No. 5,144,630). However, this system has a rather low overall UV energy conversion efficiency and the available Nd:YAG laser at high repetition rate. Diode-pumped Nd:YAG or Nd:YLF (DPY) have not yet been converted into the UV (210–213) nm ranges with useful energy level for PRK procedures. Moreover the DPY technology is limited by the high-cost of the pumping diode array and the output quality and pulsewidth of the Nd:YAG (or Nd:YLF) fundamental beam. To achieve useful UV power for PRK procedures , (100–200) mW, one should require the fundamental beam to have a very good beam quality (at least 90% Gaussian and beam divergence of smaller than 3 mrad), short pulse duration (less than 15 nanosecond) and high repetition rate (higher than 150 Hz).

SUMMARY OF THE INVENTION

In light of the above, it is an object of the present invention to provide refractive laser systems which offer the advantages of: low-cost, reduced size and weight, high reliability, easy to operate and maintain. Another object of this invention is to provide a computer-controlled scanning device which only requires low UV energy and such that all solid-state lasers becomes possible for use in PRK and other refractive surgeries currently performed only by excimer (ARF) laser and an Argon-laser-pumped Ti:sapphire laser.

Another object of this invention is to provide novel laser crystals and frequency up-conversion schemes producing good beam quality with short pulse duration and high repetition rate to achieve the required UV averaged power.

It is yet another object of the present invention to provide a refractive laser system which is compact, portable and insensitive to environmental conditions (such as vibration and temperature). This portable system may also be used in a mobile clinical center.

The prior U.S. Pat. No. 4,784,135 of Blum, et al. and assigned to IBM teaches the first use of ultraviolet irradiation (shorter than 200 nm) of a biological layer to cause ablative photo decomposition. This patent teaches that using a laser beam having a wavelength of 193 nm and an energy level of much greater than 10 mJ/pulse can be used to photoablate corneal tissue without the build up of excess heat. The present invention on the other hand proposes a much lower UV energy per pulse of (0.05–2) mJ on corneal surface for photoablation.

There are several prior art U.S. Patents relating to refractive surgery, or photorefractive keratectomy. U.S. Pat. No. 4,784,135 suggests the use of a UV laser with wavelengths less than 200 nm, in particular ArF laser at 193 nm, for non-thermal photoablation process in organic tissue. Devices for beam delivery and methods of corneal reshaping are disclosed in U.S. Pat. No. 5,019,074 using an erodible mask. Techniques for corneal reshaping by varying the size of the exposed region by iris or rotating disk are discussed in Marshall et al, "Photoablative Reprofiling of the Cornea Using an Excimer Laser: Photorefractive Keratectomy" Vol. a, Lasers in Ophthalmology, pp. 21–48 (1986). Tangential corneal surface ablation using ArF excimer laser or harmonics of Nd:YAG laser (at 532 and 266 nm) is disclosed in U.S. Pat. No. 5,102,409.

These prior arts of ArF excimer lasers, however, require high UV energy of (100–300 mJ) per pulse from the laser cavity or (30–40) mJ per pulse delivered onto the corneal surface, where large area corneal ablation using a beam spot size of about (4–6) mm which gives an energy density of (120–200) mJ/cm2. Moreover, the existing high power ArF excimer lasers operating at a repetition rate of (5–50) Hz will limit the practical use of the tangential ablation concept which takes 5–10 minutes for a 5 diopter corneal correction in a 5-mm optical zone. The high energy requirement of the currently used ArF excimer laser has the problems of: high-cost (in system, erodible mask and gas cost), high-maintenance cost, large size/weight and the systems are sensitive to environmental conditions, such as temperature and moisture.

More recently, the present inventor, J. T. Lin, has proposed a compact miniature-excimer laser with energy/pulse of (2–4) mJ from cavity and (0.8–1.2) mJ on corneal surface by using a scanning device. This system, however, is still a gas laser and repetition rate is limited to 100 Hz. Maintenance of this ArF laser is quite involved and energy stability is poor.

The L'Esperance U.S. Pat. No. 4,665,913 proposed a scanning ArF laser which requires a complex apparatus to select a section of the beam which is substantially uniform in density within a substantially square spot "dot". The overall efficiency would be less than 10% from the output of the laser window to the corneal surface. Based upon this patent, the successive sweep of the scan areas would always leave ridges between the sweeps. It should be noticed that this L'Esperance's patent uses overlaps between each of the scanned areas to obtain the desired ablation profiles of myopic (or other) corrections. However, the ridges between each of the successive ablated areas are very difficult to avoid if within each scanned area the ablated profiles are not substantially uniform. In fact, one should expect a very rough surface on these ablated areas in addition to the regular ridges between each overlapped zones. One of the problems found in these teachings is that it required individual ablated areas to be substantially uniform and in a round or square shape. This is very difficult to achieve. Even if perfectly uniform, a square portion of a fundamental beam is produced using a complex apparatus for beam reshaping.

The L'Esperance U.S. Pat. No. 4,665,913 does not appear to have found a suitable scanning method or an effective method of selecting a perfect beam (with uniform density and well-defined shape) which would overcome the above-described difficulties and make the proposed teaching become practical in cost and design for any clinical uses. In fact, L'Esperance's scanning method has been challenged by the Muller, U.S. Pat. No. 4,856,513, where the difficulties and problems of L'Esperance's teachings are discussed.

It is therefore a further object of the present invention to provide a method and apparatus for corneal reshaping by using a software-driven new scanning patterns which does not require substantially uniform density or a specific spot shape. Contrary to L'Esperance's teachings, which suggest that there should be a perfect boundary match among each square beams and that excessive overlap should be avoided, the present invention proposes that a large portion (50–80%) of overlap among the individual beams is necessary in order to achieve uniform ablated areas and a smooth profile without ridges. Furthermore, a low-power UV laser, (0.05–1)mJ on the corneal surface, at its bare-beam profile without any beam reshaping is sufficient to achieve a smooth ablation surface based on the method proposed in the present invention, where computer-controlled beam overlap and rotation are employed. In addition to the surface quality problems, it is also impossible for L'Esperance U.S. Pat. No. 4,665,913 to achieve any meaningful clinical results using his proposed techniques if a laser of only (2–4) mJ is available.

Therefore, another object of the present invention is to provide a new method-of beam scanning which combines beam overlap and rotation in a random distribution fashion on the ablated corneal surface such that the individual beam profiles are not critical, where the focused beam has a spot size of 0.1–0.8 mm at a very low energy level 0.05–1 mJ and at its bare-profile is delivered onto the corneal surface in an average fashion. Uniform, near flat-top ablated areas of 1–10 mm in diameter can be performed by the nonuniform starting-beam, but only when a set of specific predetermined overlap and orientation parameters are used. Portions of the theoretical background was published by the inventor, J. T. Lin, in SPIE Pro. vol. 1644, Ophthalmic Technologies II (1991), pp. 266–275.

One of the essential feature of the present invention for the photorefractive surgery processes is to use a scanning device in a laser system which has high repetition rates (50–50,000 Hz), but requires low energy, (0.01–1 mJ per pulse), which is 10 to 100 times less than that of the prior art devices. This new concept enables one to make the refractive lasers at a lower cost, smaller size and with less weight than that of prior art lasers. Furthermore, these compact lasers of the present invention are all solid-state and portable which is particularly suitable for mobile clinic uses. A new concept of UV-laser tissue ablation based on laser peak-power rather than energy is proposed such that lasers at both nanosecond and picosecond pulse duration are suitable for efficient corneal ablation. For lasers with repetition rates lower than 40 Hz, a multi-beam scanning method is proposed in the present invention for efficient ablation.

For ophthalmic applications, it is an aim of the present invention to include but not be limited to photorefractive keratectomy, epikeratoplasty, intrastroma photokeratectomy (IPK), phototherapeutic keratectomy (PTK), and laser in situ keratomileusis (LASIK).

SUMMARY OF THE INVENTION

The preferred embodiments of the basic ophthalmic surgery method uses a laser system for the ophthalmic surgery process, including: (1) a diode-pumped solid-state laser of Vanadate crystal (Nd:YVO4) which is frequency-converted by nonlinear crystals of KTP(Potassium titanyl phosphate), LBO (lithium triborate) and BBO(beta barium borate) into the fifth-harmonic at wavelength of 213 nm; (2) a frequency-converted Alexandrite (at high temperature) or Cr:LiSAF with output tunable wavelength of 193–220 nm; (3) a solid-state doubled-YAG pumped, diode-laser injected picosecond Ti:sapphire laser and frequency converted to UV wavelength of 205–215 nm.

According to one aspect of the present invention, the above-described basic lasers with frequency up converted to 193–215 nm focused into a spot size of 0.05–1 mm in diameter, where laser energy per pulse of 0.01–1 mJ is sufficient to achieve the photo-ablation threshold(PAT) energy density of 2–100 mJ/cm$^2$ depending upon the laser parameters (wavelengths and pulse duration). The prior art excimer laser uses large beam spot of 4–6 mm and require much higher laser energy (100–300 mJ) than the low-power lasers presented herein. A software-driven scanning device is used to control the ablation profiles in the present invention, whereas diaphragms or masks are used in the high-power, high-cost excimer laser. In another aspect of the present invention, novel frequency conversion schemes for efficient generation of UV wavelength are proposed including intracavity and optimal-polarization techniques. Another aspect of the invention is temperature and crystal angle-tuning controlled by feedback signals for stable UV output.

A two-dimensional translation device (in X,Y) is integrated into the above laser systems, where the laser heads are compact and light-weight and can be steered to the corneal center by the translation stages rather than moving the patient. The prior art high-powered excimer laser systems are stationary and require a three dimensional adjustable patient's chair for corneal concentration. Beam steering and scanning is very difficult for these high-power, heavy-weight excimer lasers.

The ophthalmic applications of the laser systems described herein include photorefractive keratectomy(PRK), phototherapeutic keratectomy (PTK), intrastroma photokeratectomy, and laser in situ keratomileusis (LASIK) for myopic, hyperopic, astigmatism and presbyopic corrections.

DETAILED DESCRIPTION OF THE PREFERRED EMBODIMENT

Figure 1:
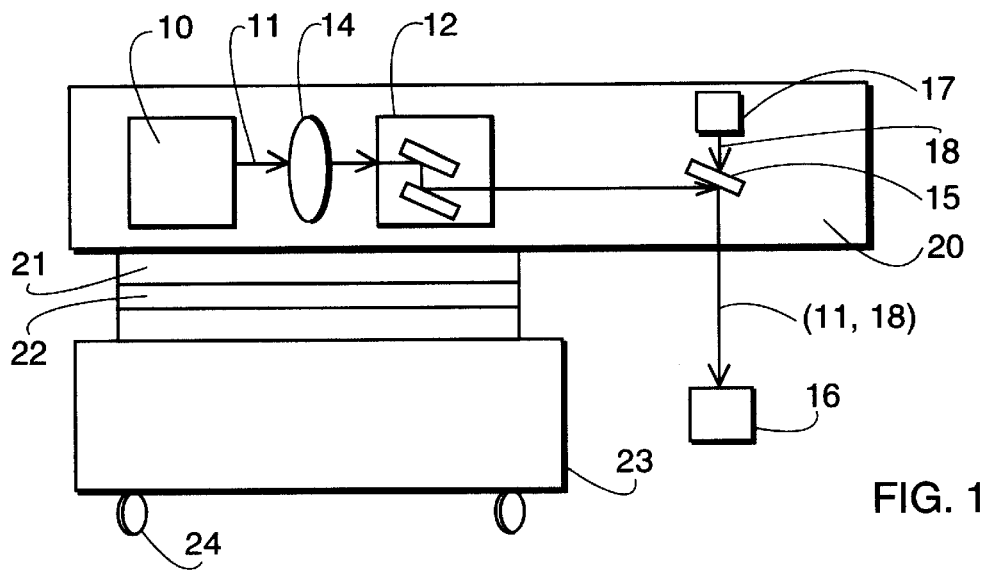
FIG. 1 is a block diagram of a computer-controlled laser system in accordance with the present invention having a laser, scanning mechanism, power supply and the beam steering stage for refractive surgeries.

The theoretical background of the present invention with regards to the beam overlap and ablation rate in PRK, PTK and LASIK procedures described in the present invention is as follows.

Given a laser energy per pulse of E (in mJ), a fluence of F (in mJ/cm2) may be achieved by focusing the beam into an area of A, where F=E/A. For corneal tissue ablation to occur requires the laser intensity I (in MW/cm$^2$) to be above the photoablation threshold (PAT), (10–100)MW/cm2 for UV-laser (193–215) nm, where I=F/t, t being the pulse duration ranging of (0.01–20) nanosecond as proposed in the present invention. Therefore it is always possible to tightly focus a pulsed-laser beam and achieve the PAT value even for a low-energy laser (0.01–1.0) mJ. The drawback of using a low-energy, small-spot laser for PRK procedures is that the operation time will be longer than that of a large-spot but high-power laser. However, time of operation may be shortened by using a high-repetition-rate laser (higher than 100 Hz). Small-spot, low-energy lasers for large area (5–9 mm) optical zone PRK procedures is clinically practical under two criteria: (i) a scanning device is used in a high-repetition-rate laser, and (ii) uniform surface ablation profile can be assured by the appropriate beam overlap. These two important issues are the basis of the new concept presented in the present invention.

In some commercial solid-state laser systems the repetition rate is limited to 50–100 Hz but have UV energy per pulse of 3–5 mJ. The preferred embodiment in this invention to speed up the laser ablation procedure is to use a multi-beam scanning device, where the main beam is split into two (or more) beams, each one will have energy of 1.5–2.5 mJ. The "effective" laser repetition rate on the corneal surface will be multiplied in a multiple beams scanning.

I have tested the corneal ablation rate of UV lasers for both nanosecond (n.s.) and picosecond (p.s.) systems. The results indicated the following ablation at various laser pulse duration and these are the basis of the present concept of photoablation threshold(PAT):

PAT=(2.5–3.5)mJ/cm2, for 25 p.s. laser and
=(50–60)mJ/cm2, for 10 n.s laser where UV lasers wavelength of 209 nm (from harmonic of Nd:YLF) and 213 nm (from harmonic of Nd:YAG) are used, respectively. For the p.s.laser, UV energy (on the corneal surface) was only 0.03 mJ and focused to a small spot size of about 0.06 mm. For the n.s. laser, energy per pulse of (0.9–1.2) mJ was used and a spot size of (0.6–0.8) mm on the corneal surface. These new concepts of photoablation at very low energy/pulse (0.03–1.2 mJ) are based upon the ablation peak-power (or intensity) rather than the laser energy. In addition to the ablation threshold (governed by laser intensity), procedure speed (governed by laser averaged power) is another important concept.

The overall operation rate (R) for a given diopter correction (D) is limited by the laser scanning rate (R1) which is in turn limited by the laser repetition rate. In addition, R is also proportional to the tissue ablation rate (RT) which is proportion to the laser averaged power (P) at a given energy E and pulse duration. The overall ablation time (T) needed of a corneal reshaping procedure follows the scaling law of: (J. T. Lin, Optical Engineering, Vol. 34, 1995)

T=DW/P, where D and W are the correction diopter and the ablation zone size, P (in mW) is the laser power on the corneal surface.

It is important to note that given an averaged power, P, the laser intensity must be above the photo-ablation threshold (PAT) by either beam focusing or by increasing the laser energy and also keeping the laser pulse short (less than 20 n.s. preferred).

Based upon this theory, I have concluded: (i) continuous wave UV lasers with low intensity normally cannot cause photo-ablation since the peak power density is much lower than the PAT value even under a tightly focused condition; (ii) UV lasers at Q-switched or mode-locked mode and with pulse-duration shorter than 20 nanosecond will normally achieve the intensity above the PAT even at low-energy level of (0.05–2)mJ. In particular, picosecond lasers at high repetition rate are desirable where energy in the microjoule range would be sufficient. Moreover, the Q-switched short pulse lasers clinically cause a much smaller thermal damage than that of a long-pulse or free-running laser. Therefore, the cost-effective refractive lasers are those which have high repetition rate (50 Hz and up) but operated at low-energy (0.05–2 mJ) and short pulse duration (0.01–20 nanoseconds).

The preferred embodiments disclosed herein in FIG. 1 are based upon this theory. Beam focusing and scanning are always required to achieve the PAT and smooth ablation profile. The individual beam profile in the scanning system is not as critical as that of prior arts systems which require a uniform overall profile within the large ablation zone of 4–6 mm. In laboratory tests, I have achieved very smooth ablation profiles with zone diameter up to 9 mm starting from a 90% Gaussian beam profile which was randomly scanned over the ablation zone. Using overlap of 50–80% of the focused beam spot of 0.2–0.8 mm, and a typical number of pulses delivered to the corneal surface of 2,000–4,000, assures a sufficient beam overlap and averaging for smooth profile. Moreover the pulse to pulse energy fluctuation is not critical in this scanning mode.

Referring to FIG. 1, a refractive laser system in accordance with the present invention comprises a basic laser 10 having a UV (193–220 nm) wavelength 11 coupled by a scanning device 12 and has the beam from focusing optics 14 directed onto a reflecting mirror 15 and onto target 16. The target 16 may be the cornea of an eye. An aiming system 17 has a visible wavelength (from a laser diode or He—Ne laser) 18 adjusted to be collinear with the ablation beam 11 and defines the centration of the beam onto the cornea surface at normal incident. The basic laser head 20 is steered by a motorized stage for X and Y horizontal directions 21 and the vertical (height) direction 22 which assures the focusing beam spot size and the centration of the beam onto the cornea. The system has a computer controlled panel 23 and wheels 24 for portable uses. The target 16 includes a human cornea for applications of PRK, PTK and LASIK. The computer controlling panel 23 also provides the synchronization between the scanning gavo (galvanometer scanner) and the laser repetition rate. A commercially available galvanometer scanner made by General Scanning, Inc. is used in scanning the laser beam.

Still referring to FIG. 1, the basic laser 10, according to the present invention, includes a compact, optically-pumped (either flash-lamp or laser-diode pumped) laser of new Vanadate crystals, including Nd:YVO$_4$, with pulse duration of 0.05–20 nanoseconds and repetition rate of 1–10,000 Hz. It is known that this basic laser 10 is available using a standard Q-switch or mode-lock where the UV wavelength at 213 nm may be achieved by the frequency conversion techniques using nonlinear crystals disclosed in my prior U.S. Pat. No. 5,144,630. The UV laser energy required for efficient ablation ranges from 0.01 mJ to 1 mJ. This new Vanadate crystal of Nd:YVO$_4$ offers some advantages over traditional hosts (such as Nd:YAG) for diode pumped systems, including a high absorption coefficient at the pump wavelength and a large stimulated emission cross section and a high inversion density to provide a very high gain, resulting in short Q-switched pulse durations even at high repetition rates of 10–50 KHz. The pulse energies at high repetition rate are higher than can be achieved with more traditional hosts, due to a short upper state lifetime that allows a fast recovery of the excited state population. The fast recovery also enhances the pulse to pulse stability of the laser at high rates. This new crystal of Nd:YVO$_4$ provides short, energetic pulses of high spatial quality which are essential for efficient harmonic generation of UV at 213 nm and the high repetition rate is also desirable for fast refractive surgery procedures.

These unique features of diode-pumped vanadate crystal make it possible for us to achieve the required UV power and energy for refractive surgeries. In prior U.S. Pat. No. 5,144,630, a diode-pumped Nd:YAG was proposed which PRK procedures had the drawbacks of long pulse duration, particularly at repetition rates over 5 KHz. The long pulse, (20–30 n.s.), significantly reduces the harmonic conversion efficiency in comparing with the short pulse, (5–10 n.s. system of Nd:YVO$_4$).

Figure 2:
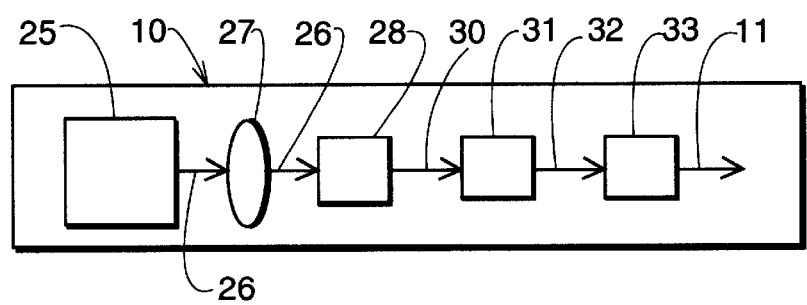
FIG. 2 is a block diagram of a laser system of FIG. 1 having a two-beam scanning mechanism.

The basic laser also includes frequency-converted lasers of optically-pumped Alexandrite or Cr:LiSAF, where efficient nonlinear crystals (as shown in FIG. 2) may be used to convert the fundamental wavelength (770–880 nm) into its fourth-harmonic at the UV tunable wavelength of 193–220 nm with energy of 0.01–2.0 mJ, repetition rate of 1–10,000 and pulse duration of 0.05–50 nanoseconds. Only two nonlinear crystals are needed in this case and overall efficiency is higher than that of the fifth harmonic generation which requires three nonlinear crystals. The basic laser may also include ultrashort pulsed lasers, such as a commercialized mode-locked, regenerative Ti:sapphire laser or other solid-state laser, with wavelength ranges of 750–1100 nm, repetition rates of 0.01–100 MHz, energy per pulse of 1–100 microjoules, and a spot size of 0.05–0.2 mm to achieve the ablation threshold. One of the preferred embodiments of the Ti:sapphire laser is to use doubled-Nd:YAG as the pump and with the sapphire cavity injection seeded by a pulsed diode laser at wavelength of 830–845 nm. The preferred diode-pumped Alexandrite laser crystal should be operated at high temperature (980–100 degrees centigrade) to produce fundamental wavelength red-shifted to 830–840 nm range for efficiency harmonic generation of UV wavelength (207–210 nm).

Still referring to FIG. 1, the scanning device 12 is synchronized with the laser repetition rate, where the computer software is capable of providing predetermined patterns according to a patient's corneal topography for the corrections of myopia, hyperopia and astigmatism. Astigmatic correction, in particular, is difficult to perform in prior art systems using a non-scanning diaphragm but can be easily achieved by the present invention using a scanning device. Furthermore, a multi-zone procedure for high diopter (6–15) changes can be performed by the computer program rather than that of the conventional mechanical iris. The scanning device 12 can also be controlled such that the reference position will follow the eye motion provided by the feedback signal from an eye tracker, where a video camera is integrated into the microscope.

The low energy laser systems described in the present invention are able to perform the refractive surgery procedures which normally require high power lasers where a scanning device is not used to assure the uniform corneal ablation by beam overlap and the ablation threshold is achieved by beam focusing. A typical beam overlap of (60–80)% is needed for smooth averaged ablation profiles on the corneal surface. Furthermore beam spinning or rotation in directions for each ablation layers is required for best surface quality. The scanning pattern controlled by the computer can be linear or circular or their combination depending on the applications of myopic, hyperopic or astigmatism. The preferred embodiments are: circular pattern for hyperopia and linear pattern for myopia and astigmatism. The basic lasers presented in this invention all are solid-state lasers with a very good beam quality laser required for efficient frequency conversion. However, the beam uniformity with flat-top profile needed in most high-power excimer lasers, is not required when the scanning device is employed. My data indicated that very smooth surface ablation profiles in PMMA plastic sheet were achieved by Gaussian profile with the scanning averaging process.

Referring to FIG. 2, a preferred embodiment for the basic laser 10 of FIG. 1 having a UV wavelength includes a diode-pumped Nd:YVO4 (Vanadate) 25 having a fundamental wavelength 26 at 1064 nm and is focused by a lens 27 into a doubling crystal 28 (KTP, LBO or BBO) to generate a green wavelength 30 at 532 nm. The green beam 30 is further converted by a fourth (or third) harmonic crystal 31 (BBO or LBO) to generate a UV wavelength 32 at 266 nm (or 355 nm) which is finally converted by a fifth harmonic crystal 33 to generate the UV wavelength 11 at 213 nm. From a commercially available diode-pumped Nd:YVO4 laser (operated at 10 KHz), I can achieve the UV (at 213 nm) energy of 0.1–0.2 mJ per pulse with average-power of 100–200 mW delivered to the corneal surface. This energy level when focused into a spot size of 0.2–0.3 mm is sufficient to ablate the corneal tissue. This diode-pumped fifth harmonic Nd:YVO$_4$ system provides the most compact refractive UV solid-state laser available today with the advantages of high UV efficiency lifetime, low-maintenance, portable and absence of toxic gas in comparison with the PRK excimer lasers currently used.

Figure 3:
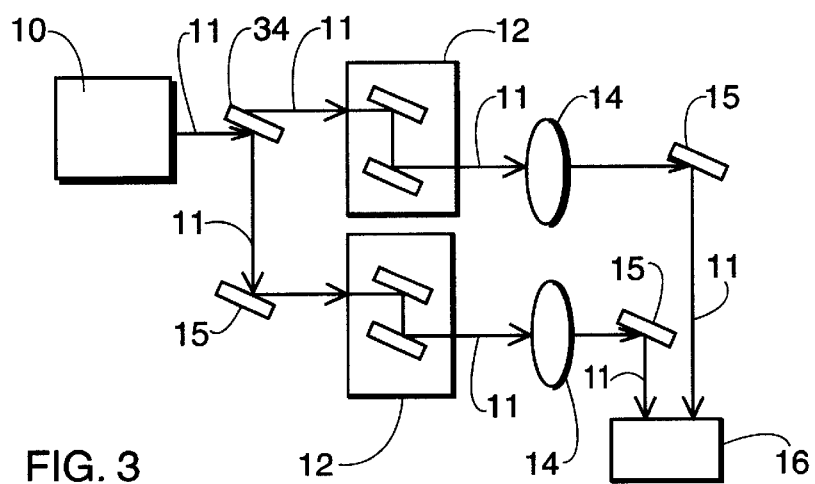
FIG. 3 is a block diagram of a laser system for the generation of ultraviolet wavelengths at 213 nm using nonlinear crystals in a diode-pumped Vanadate crystal operated at (5–10) KHz.

Referring to FIG. 3, a block diagram is presented for a two-beam scanning device in which the "effective" repetition rate is twice that of the single-beam. For example, given a basic laser operated at 50 Hz and having UV energy per pulse of 4 mJ, this two-beam device with the split beam will have 2 mJ energy each at an "effective" repetition rate of 50×2=100 Hz when the two beams are applied on a corneal surface separated by 0.01 seconds. Similarly, the basic beam may be split into 4 beams at 1 mJ each and results in an "effective" repetition rate of 50×4=200 Hz. This multi-beam scanning device is particularly useful for laser systems which are limited by repetition rate but have energy after converted into UV wavelength, more than what is typically required range of 0.05–1.0 mJ for pulse duration of 0.02–10 n.s.

Still referring to FIG. 3, the basic laser 10 is converted into a UV wavelength 11 which is equally split into two beams by a beam splitter 34, one of which is reflected by a 45-degree reflector 15 into the scanning pair 12. Each scanning beam is focused by an adjusted focal length 14 and reflected by reflector 15 prior to the corneal surface 16. Each of the scanning pair 12 is software-driven and one beam is delayed by half-pulse to the other when it arrives on the corneal surface 16. In addition to the multi-beam scanning device, the concept of effective repetition rate may be achieved also by combining two basic lasers each having a repetition rate of, for example, 50 Hz. By delaying these two lasers on the corneal surface of 0.01 second, you can obtain an effective repetition rate of 50×2=100 Hz.

Some novel frequency conversion systems are illustrated which provide a significant improvement on the conversion efficiency for the generation of UV sources from infrared lasers.

Figure 4A:
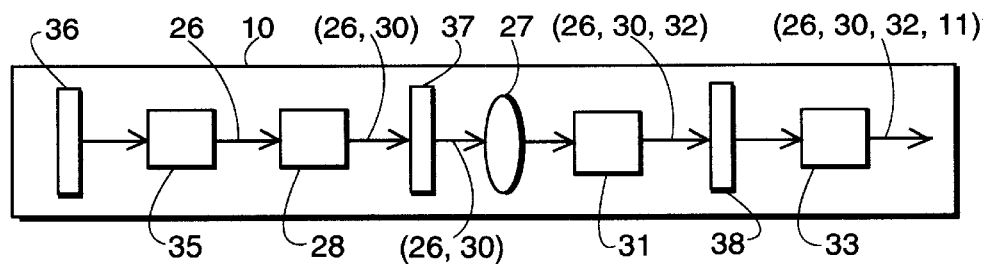
FIGS. 4(a), 4(b) and 4(c) are block diagrams for various frequency conversion systems.

The first system is presented in FIG. 4A. The basic UV laser 10 is generated from a fundamental solid-state laser using a laser crystal 35 includes but not limited to neodymium-doped ytttrium-based or vanadium-based crystals, Cr:LiSAF and alexandrite crystals. In the following discussion, the laser crystal of Nd:YAG and Nd:YVO$_4$ is used as an example, since they have almost the same fundamental wavelength of 1064 nm. The fundamental wavelength 26 is converted into the green (532 nm) beam 30 by a doubling crystal 28 in an intracavity doubling scheme which consists of a back mirror 36 coated at high-reflection (HR) of 1064 nm and a front mirror 37 coated at HR at 1064 nm and high-transmission (HT) at 532 nm in one surface and HT at 532 nm for the other surface. These two beams 26 and 30 are then focused by a lens 27 into a mixing crystal 31 for third harmonic-beam 32 at 355 nm which is further mixed with the green beam 30 by the fifth harmonic crystal 33 to generate the UV beam 11 at 213 nm. The preferred embodiment is to use a type-II third harmonic crystal 33 and by using a polarization rotator 38 in order to meet the correct polarization directions in a type-I fifth harmonic crystal 33. The mixing of 355 nm and 532 nm is more efficient and stable than that of the prior art which proposed a mixing of 1064 nm and 266 nm to obtain the 213 nm.

Figure 4B:
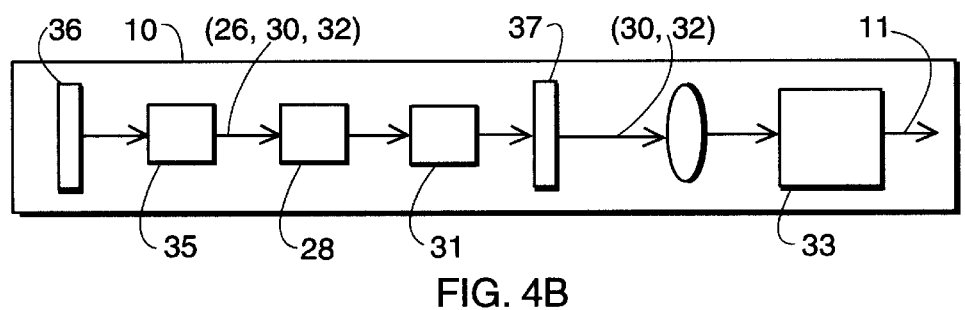

Referring to FIG. 4B, the mixing crystal 31 is now integrated inside the cavity with the front mirror 37 coating modified into HR at 1064 and 532 on one surface and HT at 355 nm on another surface. In this two-crystal intracavity generation, only one mixing crystal 33 is needed outside the cavity to produce the UV beam 11. We note that this scheme will provide a very efficient conversion for the generation of both green (532 nm) and UV (355 nm) such that the overall efficiency of 213 nm may increase at lease 30% in comparison that of a conventional external cavity. Furthermore, the basic laser system will be more compact and easy in alignment, since there is only one crystal inside the cavity which requires a fine adjustment.

Figure 4C:
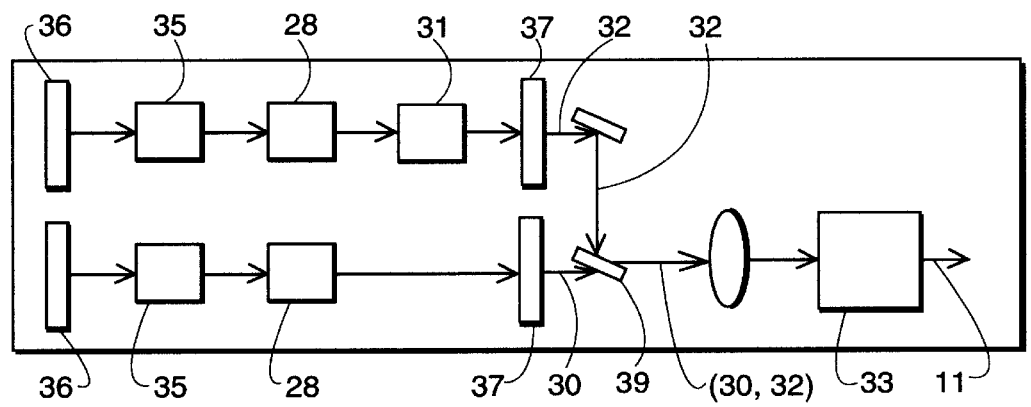

A combination of systems of FIGS. 4A and 4B provides the advantages of high overall efficiency of UV (213 nm) with only small fundamental beam energy needed in each basic laser. This is presented in FIG. 4C, where the UV beam 32 (at 355 nm) is combined by a polarization-controlled optics 39 with the green beam 30 and focused into a fifth harmonic crystal 33.

Figure 5:
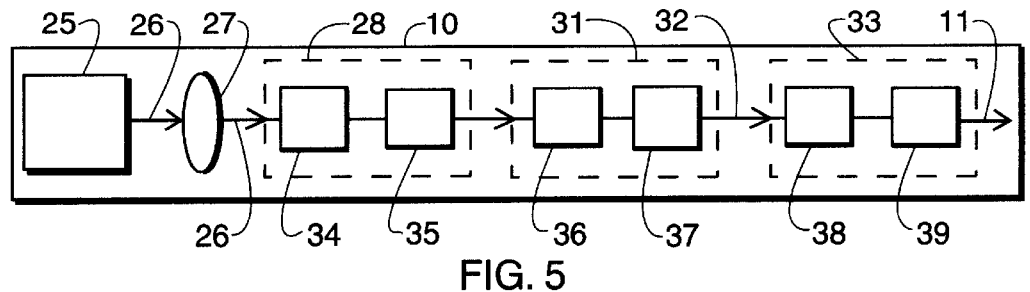
FIG. 5 is a block diagram for enhanced conversion efficiency by using a series of non-linear crystals for each stage.

Referring to FIG. 5, an extended diagram of FIG. 2 is shown with a plurality of non-linear crystals in each conversion stage. The doubling crystals 28 (KTP, LBO or BBO) is now extended to two crystals 34 and 35 which re combining any of the two crystals out of KTP, LBO and BBO. Similarly, the third harmonic crystals 31 and 33 are now extended to 36, 37, 38 and 39, which can be BBO or LBO but not KTP. I have demonstrated an efficiency conversion improvement of up to 40% by the above enhanced device using two crystals in each stage in comparison with the single crystal stage case. Moreover, energy fluctuation caused by laser heating effects are largely reduced.

The basic lasers used and converted into the UV (193–213 nm) wavelength by the above-described systems include: (i) a high-power Nd:YAG laser, (made by Coherent and Continum in US), (100 Hz, 15 n.s. pulse energy of 400 mJ at 1064 nm) which will produce about 10 mJ at 213 nm for using the external cavity shown in FIG. 2 and the two-beam scanning device shown in FIG. 3 due to the low repetition rate; (ii) diode-pumped fiber-coupled Nd:YVO$_4$ laser, (made by Spectra-Physics), (10 KHz, 10 n.s. pulse at an average-power of 4–5 Watts) which will produce 100–200 mW UV beam at 213 nm average-power suitable for corneal reshaping. However, a small spot size of 0.2–0.4 mm should be used in the scanning device for efficient ablation, since the energy per-pulse of the UV 213 nm will be only 0.05–0.08 mJ limited by the available fundamental energy of 0.5–0.8 mJ and an overall UV conversion efficiency of 8%–10%. (iii) picosecond, regenerative doubled-YAG pumped Ti:sapphire laser which can be customer-made and an injection-seed diode-laser at 830–840 nm is the preferred embodiment to achieve sufficient UV (tunable 207–210 nm) energy for corneal reshaping; (iv) customer-made, compact arc-lamp-pumped Nd:YAG at 150–200 Hz with very good beam quality and energy per pulse of 40–50 mJ; which system has great advantages over the conventional high-power Nd:YAG laser with energy/pulse of 300–400 mJ but a lower repetition rate of 50–100 Hz and is not cost effective; (v) customer-made diode-pumped alexandrite laser, where the laser crystal will be operated at high temperature (about 100 degrees centigrade) in order to red-shift the fundamental wavelength to 830–840 nm range for efficient UV generation of 207–210 nm, where the conventional arc-lamp-pumped alexandrite is limited by its repetition rate of 50 Hz and the fundamental wavelength is too short (less than 820 nm at room temperature) to covert into the suitable UV range of (207–210) nm.

The method disclosed in the present invention combines abeam scanning, overlapping and pattern rotation (randomization) provides a powerful yet simple technique for optimal outcome of laser refractive surgery which involves both clinical aspect (ablation diopter, ablation optical zone, smoothness, patient centration and operation speed) and engineering aspects (beam profile, uniformity, stability, energy, spot size and delivery systems).

The concept of achieving a smooth ablation surface by using the randomly rotated scanning pattern as disclosed herein needs a microsensor (made by TENCOR) to measure the PMMA profiles. Using the scanning device as described in the present invention, I have analyzed a great number of ablated PMMA and have concluded the optimum parameters for laser spot size, energy and overlap as disclosed herein.

While the invention has been shown and described with reference to the preferred embodiments thereof, it will be understood by those skilled in the art that the foregoing and other changes and variations in form and detail may be made therein without departing from the spirit, scope and teaching to the invention. Accordingly, threshold and apparatus, the ophthalmic applications herein disclosed are to be considered merely as illustrative and the invention is to be limited only as set forth in the claims.

What is claimed is:

1. A method for performing ophthalmic surgery comprising:
   providing a basic laser having a pulsed output laser beam of a fundamental ultraviolet wavelength within a range of 193–220 nm exiting from an output window of said basic laser, a repetition rate of 1 Hz to 1000 Hz, and an energy level exiting from said output window of said basic laser of no greater than 10 mJ per pulse;
   applying said pulsed laser beam onto corneal tissue; and
   scanning said pulsed laser beam in a substantially overlapping pattern on said corneal tissue such that adjacent ablation spots on a single ablation layer of said corneal tissue significantly overlap one another.

2. The method for performing ophthalmic surgery according to claim 1, wherein:
   said substantially overlapping pattern is achieved using randomized scanning of said pulsed laser beam on said corneal tissue.

3. The method for performing ophthalmic surgery according to claim 1, wherein:
   said pulsed laser beam has a spot size on said corneal tissue of no greater than 1 mm.

4. The method for performing ophthalmic surgery according to claim 1, wherein:
   pulses of said pulsed laser beam corresponding to adjacent ablation spots on said single ablation layer overlap one another by least 50 percent.

5. The method for performing ophthalmic surgery according to claim 1, wherein:
   said pulsed laser beam is scanned synchronously with said pulses of said pulsed laser beam.

6. The method for performing ophthalmic surgery according to claim 1, wherein:
   an area of corneal tissue 0.05 to 0.5 microns deep is removed with each pulse of said pulsed laser beam.

7. The method for performing ophthalmic surgery according to claim 1, wherein:
   said pulsed laser beam is scanned in circular patterns.

8. The method for performing ophthalmic surgery according to claim 1, wherein:
   said pulsed laser beam is scanned in linear patterns.

9. A method for ablating tissue, comprising:
   providing a basic laser having a pulsed output laser beam of a fundamental ultraviolet wavelength of 193 nm exiting from an output window of said basic laser, and a repetition rate of 1 Hz to 1000 Hz; and
   scanning said pulsed output beam into a substantially overlapping pattern of beam pulses on said tissue such that adjacent ablation spots on a single ablation layer of said corneal tissue significantly overlap one another.

10. The method for ablating tissue according to claim 9, wherein:
    said substantially overlapping pattern of beam pulses has an orientation which is achieved using a randomized scanning of said pulsed output beam on said tissue.

11. The method for ablating tissue according to claim 9, wherein:
    said pulsed output laser beam has an energy level exiting from said output window of said basic laser of no greater than 10 mJ per pulse.

12. The method for ablating tissue according to claim 9, wherein:
    said scanning overlaps adjacent beam pulses corresponding to adjacent ablation spots on said single ablation layer by at least 50 percent.

* * * * *